United States Patent [19]

Born et al.

[11] Patent Number: 5,306,436

[45] Date of Patent: Apr. 26, 1994

[54] NEW PHOSPHOSULFIDES COMPOUNDS AND USE THEREOF AS OIL LUBRICANTS

[75] Inventors: Maurice Born, Nanterre; Ourida Aberkane, Fameck; Jean-Luc Mieloszynski, Montigny les Metz; Daniel Paquer, Vandoeuvre; Guy Parc, Rueil Malmaison, all of France

[73] Assignee: Institut Francais du Petrole, Rueil Malmaison, France

[21] Appl. No.: 749,783

[22] Filed: Aug. 26, 1991

[30] Foreign Application Priority Data

Aug. 24, 1990 [FR] France ................... 90 10702
Dec. 27, 1990 [FR] France ................... 90 16530

[51] Int. Cl.$^5$ ............... C10M 137/10; C10M 137/06; C07F 9/165
[52] U.S. Cl. ................ 252/32.7 E; 252/46.6; 252/46.7; 556/18; 556/25; 558/165; 558/177; 558/186
[58] Field of Search ............ 556/18, 25; 558/165, 558/177, 186, 165, 177, 186; 252/32.7 E, 46.6, 46.7

[56] References Cited

U.S. PATENT DOCUMENTS

| | | | |
|---|---|---|---|
| 2,750,342 | 6/1956 | Mikeska et al. | 558/186 X |
| 3,029,268 | 4/1962 | Goldsmith | 558/186 X |
| 4,766,228 | 8/1988 | Born et al. | 558/165 X |

*Primary Examiner*—Mary C. Lee
*Assistant Examiner*—Michael G. Ambrose
*Attorney, Agent, or Firm*—Millen, White, Zelano & Branigan

[57] ABSTRACT

Useful as additive for lubricating oils are novel phosphosulphur compounds in accordance with the general formula (I):

$$(((R^1-S_x-O_y-A-)_rB_v)_pP(X)-Y_t-)_qZ_m$$

in which e.g. $R^1$ represents an alkyl or alkenyl group, A represents the group $-(CH_2)_n-O-$, B represents the group $-P(S)-S-CH_2-(CH_3)-O-$, X represents an oxygen atom or a sulphur atom, Y represents an oxygen atom, a sulphur atom or an oxygen or sulphur-containing hydrocarbon chain, Z represents a hydrogen, chlorine or sulphur atom, a polysulphide chain, a metal or an alkyl or alkenyl group, $x=1,2$ or 3, $y=0$, 1 or 2, v is 0 or 1, r is 1 (if $v=0$) or $r=2$ (if $v=1$), $p=2$ or 3, $t=0$ or 1, $m=0,1$ or 2, $q=$ the valency of Z if Z is a metal or $q=1$ or 2 and n is an integer from 1 to 30.

20 Claims, No Drawings

NEW PHOSPHOSULFIDES COMPOUNDS AND USE THEREOF AS OIL LUBRICANTS

BACKGROUND OF THE INVENTION

The present invention relates to novel phosphosulphur compounds (i.e. sulphur and phosphor-containing) and their use as petroleum additives, particularly as antioxidant, antiwear, extreme-pressure and anticorrosive additives for lubricating oils.

Antiwear and extreme-pressure additives have been used for decades particularly in engine oils, transmission fluids and hydraulic fluids. Numerous additive types have been developed and several of them have made it possible to very significantly reduce deterioration to mechanisms and therefore extend their life.

Among the antiwear and extreme-pressure additives the most active and therefore the most significantly industrially developed have been dialkyl and diaryl dithiophosphates and metallic dialkyl dithiocarbamates, (particularly those of zinc), alkyl thiophosphates, tricresyl phosphate, didodecyl phosphate, sulphurized terpenes, sulphur-containing spermaceti oil and various chlorine compounds. Certain of them are described in U.S. Pat. Nos. 2,364,283, 2,364,284, 2,365,938, 2,410,650, 2,438,876, 3,190,833. These are generally compounds containing heteroatoms such as sulphur and phosphorus, either alone (e.g. tricresyl phosphate, sulphur-containing terpenes and dithiocarbamates) or in combination (e.g. metallic dialkyl dithiophosphates and alkyl thiophosphates). Reference can be made to French Patents FR-A-982 719 and 1 321 821 and U.S. Pat. Nos. 2,750,342 and 3,944,495.

The phosphosulphur compounds used previously have relative sulphur and phosphorus quantites which are imposed by the stoichiometry of the reactions during their synthesis and which in particular give them antiwear and extreme-pressure properties, which cannot be modified by the Expert.

SUMMARY OF THE INVENTION

Novel phosphosulphur compounds have now been discovered, which can be used as lubricating additives, preferably prepared by the reaction of conventional phosphor-containing reagents with (poly)sulphurized alcohols, which makes it possible to modify at random the relative antiwear and extreme-pressure performances of said phosphosulphur compounds.

The phosphosulphur compounds according to the invention are in accordance with the general formula (I):

$$(((R^1-S_x-O_y-A-)_rB_v-)_pP(X)-Y_t-)_qZ_m$$

in which $R^1$ represents an alkyl group (e.g. methyl, ethyl or tert. butyl) or alkenyl group (e.g. $CH_2=C(CH_3)-CH_2-$), which may or may not be functionalized, containing 1 to 30 carbon atoms; A represents the group $-(CH_2)_n-O-$ or the group

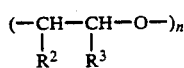

in which n is an integer from 1 to 30 and $R^2$ and $R^3$, which can be the same or different, each represent a hydrogen atom or a substantially hydrocarbonated monovalent radical with 1 to 30 carbon atoms (e.g. methyl, ethyl, etc.), $R^2$ and $R^3$ can be interlinked to form a polymethylene chain and in general A represents the group $-(CH_2)_n-O-$; B represents the group

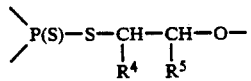

in which $R^4$ and $R^5$, which can be the same or different, in each case represent a hydrogen atom or a substantially hydrocarbonated monovalent radical with 1 to 30 carbon atoms and $R^4$ and $R^5$ can be interlinked to form a polymethylene chain; e.g. $R^4=H$ and $R^5=H$ or $CH_3$; X represents an oxygen atom or a sulphur atom; Y represents an oxygen atom, a sulphur atom or a sulphur or oxygen-containing hydrocarbon chain; Z represents a hydrogen atom, a chlorine atom, a sulphur atom, a polysulphurized chain, a metal chosen e.g. from among the group formed by sodium, zinc, copper, molybdenum, lead, antimony and cadmium, an oxygen or sulphur-containing derivative of molybdenum or an alkyl, alkenyl or $R^6$ group, which may or may not be functionalized, containing 1 to 30 carbon atoms; x is an integer equal to or greater than 1 and preferably equal to 1,2 or 3; y is equal to 0,1 or 2 and if y=0 then $(R^1-S_x-O_y-A-)_r$ is written $(R^1-S_x-A-)_r$; v is equal to 0 or 1 (if v=0 there is then no B group in the formula of compounds according to the invention); r is equal to 1 if v=0 and r is equal to 2 if v=1; p is equal to 2 or 3; t is equal to 0 or 1 (if t=0 then there is no Y group in the formula of compounds according to the invention); m is equal to 0 or 1 (if m=0 then there is no Z group in the formula of compounds according to the invention); and q is an integer equal to the valency of Z if Z is a metal or a number equal to 1 or 2.

In the definition of $R^1$ and $R^6$, the term functionalized group is understood to mean a group containing at least one heteroatom such as e.g. chlorine or sulphur, or at least one chemical function e.g. chosen from among the carboxylic, aldehyde, ketone, nitrile, hydroxyl and epoxide functions, whereby several of these functions can be present in the same $R^1$ and $R^6$ group.

The different types of phosphosulphur compounds according to the invention are preferably as follows (the term (poly)sulphurized means that the compound is either monosulphurized (x=1) or polysulphurized (x>1)):

polysulphurized dialkyl dithiophosphoric and dialkenyl dithiophosphoric acids of general formula (II):

$$(R^1-S_x-(CH_2)_n-O-)_2P(S)-SH$$

i.e. of general formula (I) in which $A=-(CH_2)_n-O-$, X=S, Y=S, Z=H, y=0, v=0, r=1, p=2, t=1, q=1 and m=1; moreover in formula (II) x is a number equal to or greater than 2 and as examples of compounds of formula (II) reference can be made to those for which $R^1$=tert. butyl, x=2, n=2,3,4,5 or 6 and preferably n=2,3 or 6 and $R^1=CH_2=C(CH_3)-CH_2-$, x=2, n=2,3,4,5 or 6 and preferably n=3;

(poly)sulphurized alcohols of general formula (III):

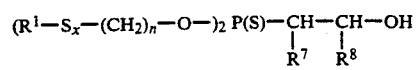

in which $R^7$ and $R^8$, which can be the same or different, in each case represent a hydrogen atom or a substantially hydrocarbon-containing monovalent radical with 1 to 30 carbon atoms and $R^7$ and $R^8$ can be interlinked to form a polymethylene chain; formula (III) corresponding to general formula (I) in which $A=—(CH_2)_n—O$, $X=S$, $Y=S$,

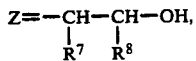

$y=0$, $v=0$, $r=1$, $p=2$, $t=1$, $q=1$, $m=1$; moreover, in formula (III), x is a number equal to or greater than 1; examples of compounds of formula (III) being those for which $R^1=$tert. butyl or $CH_2=C(CH_3)—CH_2—$, $x=1$ or 2, $n=2,3,4,5$ or 6, $R^7=H$ and $R^8=H$ or $CH_3$;

the polysulphurized metal salts of general formula (IV):

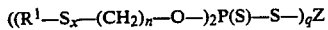

in which Z is a metal and q is a number equal to the valency of Z, i.e. of general formula (I) in which $A=—(CH_2)_n—O—$, $X=S$, $Y=S$, Z is a metal (e.g. zinc) $y=0$, $v=0$, $r=1$, $p=2$, $t=1$, $q=$ valency of Z and $m=1$; moreover, in formula (IV), x is a number equal to or greater than 2, e.g. examples of compounds of formula (IV) are those for which R=tert. butyl or $CH_2=C(CH_3)—CH_2—$, $x=2$, $n=2,3,4,5$ or 6, $Z=Zn$ and $q=2$; (poly)sulphurized dihydrocarbyldithiophosphyldithiophosphoric acids and corresponding poly(sulphurized) metal salts of general formula (V):

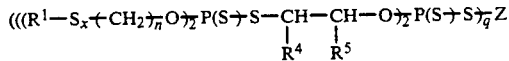

in which $Z=H$ or a metal (e.g. zinc), i.e. of general formula (I) in which $A=—(CH_2)_n—O—$, $X=S$, $Y=S$, $Z=H$ or a metal, $y=0$, $v=1$, $r=2$, $p=2$, $t=1$, $q=1$ (if $Z=H$) or q is the valency of Z (if Z is a metal) and $m=1$; moreover, in formula (V), x is a number equal to or greater than 1; examples of compounds of formula (V) being those for which $R^1=$tert. butyl or $CH_2=C(CH_3)—CH_2—$, $x=1$ or 2, $n=2,3,4,5$ or 6, $R^4=H$, $R^5=H$ or $CH_3$, $Z=Zn$ (and $q=2$) or $Z=H$ (and $q=1$);

(poly)sulphurized organic compounds of general formula (VI):

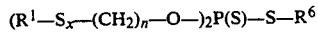

i.e. of general formula (I) in which $A=—(CH_2)_n—O—$, $X=S$, $Y=S$, $Z=R^6$, $y=0$, $v=0$, $r=1$, $p=2$, $t=1$, $q=1$ and $m=1$; moreover, in formula (VI), x is a number equal to or greater than 1 and $R^6$ is the monovalent radical of an alcohol $R^6$—OH; examples of compounds of formula (VI) are those for which $R^1=$tert. butyl or $CH_2=C(CH_3)—CH_2—$, $x=1$ or 2, $n=2,3,4,5$ or 6 and $R^6=(CH_3)_3—C—S—(CH_2)_3—CH_2—$;

(poly)sulphurized organic compounds of general formula (VII):

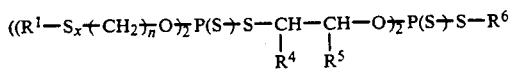

i.e. of general formula (I), in which $A=—(CH_2)_n—O—$, $X=S$, $Y=S$, $Z=R^6$, $y=0$, $v=1$, $r=2$, $p=2$, $t=1$, $q=1$ and $m=1$; moreover, in formula (VII), x is a number equal to or greater than 1; examples of compounds of formula (VII) being those for which $R=$tert. butyl or $CH_2=C(CH_3)—CH_2—$, $x=1$ or 2, $n=2,3,4,5$ or 6, $R^4=H$, $R^5=H$ or $CH_3$ and $R^6=(CH_3)_3—C—S—(CH_2)_3—CH_2—$;

polysulphurized dialkylphosphoric and dialkenylphosphoric acids and the corresponding polysulphurized metal salts of general formula (VIII):

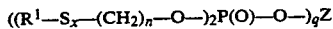

in which $Z=H$ or a metal (e.g. zinc), i.e. of general formula (I), in which $A=—(CH_2)_n—O—$, $X=0$, $Y=0$, $Z=H$ or a metal, $y=0$, $v=0$, $r=1$, $p=2$, $t=1$, $q=1$ (if $Z=H$) or q is the valency of Z (if Z is a metal) and $m=1$; moreover, in formula (VIII) x is a number equal to or greater than 2 and examples of compounds of formula (VII) are those for which $R^1=$tert. butyl or $CH_2—C(CH_3)—CH_2—$, $x=2$, $n=2,3,4,5$ or 6, $Z=Zn$ (and $q=2$) or $Z=H$ (and $q=1$);

(poly)sulphurized dihydrocarbyldithiophosphylphosphoric acids and the corresponding (poly)sulphurized metal salts of general formula (IX):

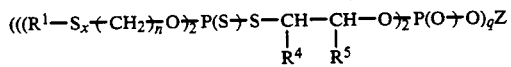

in which $Z=H$ or a metal (e.g. zinc), i.e. of general formula (I) in which $A=—(CH_2)_n—O—$, $X=0$, $Y=0$, $Z=H$ or a metal, $y=0$, $v=1$, $r=2$, $p=2$, $t=1$, $q=1$ (if $Z=H$) or q is the valency of Z (if Z is a metal) and $m=1$; moreover, in formula (IX), x is a number equal to or greater than 1; examples of compounds of formula (IX) are those for which $R^1=$tert. butyl or $CH_2=C(CH_3)—CH_2—$, $x=1$, $n=2,3,4,5$ or 6, $R^4=H$, $R^5=H$ or $CH_3$, $Z=Zn$ (and $q=2$) or $Z=H$ (and $q=1$);

polysulfurized dialkylchlorophosphates and dialkenylchlorophosphates of general formula (X):

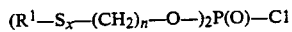

i.e. of general formula (I) in which $A=—(CH_2)_n—O—$, $X=0$, $Z=Cl$, $y=0$, $v=0$, $r=1$, $p=2$, $t=0$, $q=1$ and $m=1$; moreover, in formula (X), x is a number equal to or greater than 2; examples of compounds of formula (X) being those for which $R^1=$tert. butyl or $CH_2=C(CH_3)—CH_2—$, $x=2$, $n=2,3,4,5$ or 6 and preferably $n=3$ or 6;

(poly)sulphurized dialkylchlorothiophosphates and dialkenylchlorothiophosphates of general formula (XI):

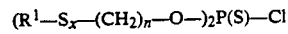

i.e. of general formula (I) in which $A=—(CH_2)_n—O—$, $X=S$, $Z=Cl$, $y=0$, $v=0$, $r=1$, $p=2$, $t=0$, $q=1$ and $m=1$; moreover, in formula (XI), x is a number equal to or greater than 1; examples of compounds of formula (XI) being those for which $R^1=$tert. butyl or $CH_2=C(CH_3)—CH_2—$, $x=1$ or 2, $n=2,3,5$ or 6 and preferably $n=3$ or 6;

(poly)sulphurized organic compounds of general formula (XII):

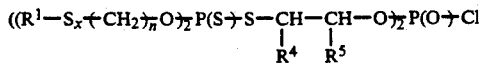

i.e. of formula (I) in which $A=-(CH_2)_n-O-$, $X=0$, $Z=Cl$, $y=0$, $v=1$, $r=2$, $p=2$, $t=0$, $q=1$ and $m=1$; moreover, in formula (XII), x is a number equal to or greater than 1; examples of compounds of formula (XII) being those for which $R^1=$ tert. butyl or $CH_2=C(CH_3)-CH_2-$, $x=1$ or 2, $n=2,3,4,5$ or 6, $R^4=H$ and $R^5=H$ or $CH_3$;

(poly)sulphurized organic compounds of general formula (XIII):

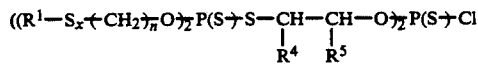

i.e. of formula (I) in which $A=-(CH_2)_n-O-$, $X=S$, $Z=Cl$, $y=0$, $v=1$, $r=2$, $p=2$, $t=0$, $q=1$ and $m=1$; moreover, in formula (XIII), x is a number equal to or greater than 1; examples of compounds of formula (XIII) being those for which $R^1=$ tert. butyl or $CH_2=C(CH_3)-CH_2-$, $x=1$ or 2, $n=2,3,4,5$ or 6, $R^4=H$ and $R^5=H$ or $CH_3$;

(poly)sulphurized trialkylphosphates and trialkenylphosphates of general formula (XIV):

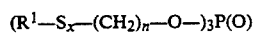

in which x is a number equal to or greater than 1, i.e. of general formula (I) in which $A=-(CH_2)_n-O-$, $X=0$, $y=0$, $v=0$, $r=1$, $p=3$, $t=0$, $q=1$ and $m=0$; examples of compounds of formula (XIV) being those for which $R^1=$ tert. butyl or $CH_2=C(CH_3)-CH_2-$, $x=1$ or 2 and $n=2,3,4,5$ or 6;

(poly)sulphurized organic compounds of general formula (XV):

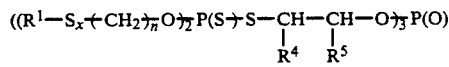

in which x is a number equal to or greater than 1, i.e. of formula (I) in which $A=-(CH_2)_n-O-$, $x=0$, $y=0$, $v=1$, $r=2$, $p=3$, $t=0$, $q=1$ and $m=0$; examples of compounds of formula (XV) being those for which $R^1=$ tert. butyl or $CH_2=C(CH_3)-CH_2-$, $x=1$ or 2, $n=2,3,4,5$ or 6, $R^4=H$ and $R^5=H$ or $CH_3$;

(poly)sulphurized trialkyl thiophosphates or trialkenyl thiophosphates of general formula (XVI):

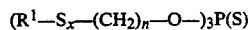

in which x is a number equal to or greater than 1, i.e. of general formula (I) in which $A=-(CH_2)_n-O-$, $X=S$, $y=0$, $v=0$, $r=1$, $p=3$, $t=0$, $q=1$ and $m=0$; and examples of compounds of formula (XVI) are those for which $R^1=$ tert. butyl or $CH_2=C(CH_3)-CH_2-$, $x=1$ or 2 and $n=2,3,4,5$ or 6;

(poly)sulphurized organic compounds of general formula (XVII):

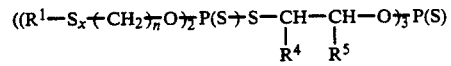

in which x is a number equal to or greater than 1, i.e. of formula (I) in which $A=-(CH_2)_n-O-$, $X=S$, $y=0$, $v=1$, $r=2$, $p=3$, $t=0$, $q=1$ and $m=0$; examples of compounds of formula (XVII) are those for which $R^1=$ tert. butyl or $CH_2=C(CH_3)-CH_2$, $x=1$ or 2, $n=2,3,4,5$ or 6, $R^4=H$ and $R^5=H$ or $CH_3$;

(poly)sulphurized dialkyl phosphonates or dialkenylphosphonates of general formula (XVIII):

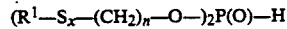

in which x is a number equal to or greater than 1, i.e. of general formula (I) in which $A=-(CH_2)_n-O-$, $X=0$, $Z=H$, $y=0$, $v=0$, $r=1$, $p=2$, $t=0$, $q=1$ and $m=1$; and examples of compounds of formula (XVIII) are those for which $R^1=$ tert. butyl or $CH_2=C(CH_3)-CH_2-$, $x=1$ or 2, $n=2,3,4,5$ or 6;

(poly)sulphurized organic compounds of general formula (XIX):

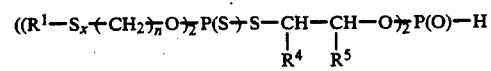

in which x is a number equal to or greater than 1, i.e. of general formula (I) in which $A=-(CH_2)_n-O-$, $X=0$, $Z=H$, $y=0$, $v=1$, $r=2$, $p=2$, $t=0$, $q=1$ and $m=1$; and examples of compounds of formula (XIX) are those for which $R^1=$ tert. butyl or $CH_2=C(CH_3)-CH_2-$, $x=1$ or 2, $n=2,3,4,5$ or 6, $R^4=H$ and $R^5=H$ or $CH_3$;

and (poly)sulphurized organic compounds of general formula (XX):

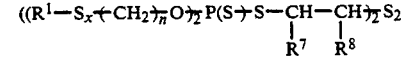

in which x is a number equal to or greater than 1 and n is a number equal to or greater than 3, i.e. of general formula (I) in which $A=-(CH_2)_n-O-$, $X=S$,

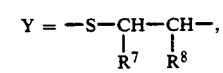

$R^7$ and $R^8$ being defined as hereinbefore, $Z=S_w$, w being a number equal to or greater than 1, $y=0$, $v=0$, $r=1$, $p=2$, $t=1$, $q=1$ and $m=1$; and examples of compounds of formula (XX) are those for which $R^1=CH_3$, $C_2H_5-$, $(CH_3)_3C-$ and $CH_2=C(CH_3)-CH_2$, $x=1,2$ or 3, $n=3,4,5$ or 6, $R^7=H$, $R^8=H$ or $CH_3$ and $w=1,2,3$ or 4; and more specifically the compounds having the following formulas (with tBu=tert. butyl):

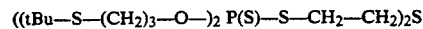

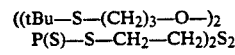

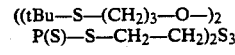

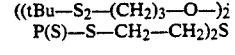

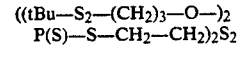

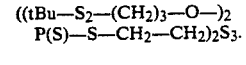

Processes for the preparation of the phosphosulphur compounds according to the invention are illustrated in the examples. More particularly due to their good antioxidant, anticorrosive and in particular antiwear and extreme pressure properties, each phosphosulphur compound according to the invention can advantageously be used as an additive for in particular mineral and/or synthetic lubricating oils at a concentration of 0.05 to 5% by weight.

Therefore the present invention relates to a lubricating composition incorporating a major proportion of lubricating oil and 0.05 to 5% by weight of at least one phosphosulphur compound according to the invention.

The following examples illustrate the invention without limiting its scope.

EXAMPLE 1

Synthesis of a monosulphurized dialkyldithiophosphoric acid (known product)

In a first stage, 3000 cm$^3$ of pure ethyl alcohol are introduced into a 6000 cm$^3$ three-necked reactor, followed by 372 g (9.3 mole) of sodium hydroxide. After dissolving, the mixture is heated to 50° C. and progressive addition takes place of 837.6 g (9.3 mole) of 2-methyl-propane-2-thiol. At the end of addition, the temperature is kept at 50° C. for a further 30 minutes, followed by cooling to 20° C. This is followed by the progressive introduction of 878.8 g (9.3 mole) of n-chloropropanol. The mixture is brought to the reflux of the alcohol for 6 hours and then cooled to ambient temperature.

The NaCl formed is eliminated by filtration and the organic solution acidified by a 2N HCl aqueous solution. The organic phase is collected and then the aqueous phase extracted by dichloromethane. The organic fractions are combined, washed with water, dried on anhydrous Na$_2$SO$_4$ and the dichloromethane is eliminated by evaporation under reduced pressure.

The product is purified by distillatiion under reduced pressure (PE=84° C./1 mmbar), which makes it possible to obtain 1370 g of a colourless product with the following elementary analysis:

| wt. % C | | wt. % H | | wt. % S | |
|---|---|---|---|---|---|
| Found (Fd) | Theory (Th) | Found (Fd) | Theory (Th) | Found (Fd) | Theory (Th) |
| 56.81 | 56.73 | 10.79 | 10.81 | 21.84 | 21.66 |

The expected chemical structure is confirmed by $^{13}$C NMR analysis, namely:

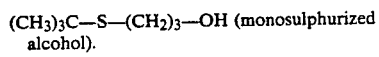
(CH$_3$)$_3$C—S—(CH$_2$)$_3$—OH (monosulphurized alcohol).

In a second stage 189.6 g (1.28 mole) of previously prepared monosulphurized alcohol and 400 cm$^3$ of chloroform are introduced into a 2000 cm$^3$ three-necked reactor. The mixture is heated to 60° C., followed by the progressive addition of 71.12 g (0.32 mole) of P$_2$S$_5$. After completely dissolving the P$_2$S$_5$, the mixture is kept for an additional hour at 60° C. and accompanied by stirring. After eliminating the chloroform under reduced pressure, 240 g of a pale yellow liquid are collected, which has the following elementary analysis:

| wt. % C | | wt. % H | | wt. % S | | wt. % P | |
|---|---|---|---|---|---|---|---|
| Fd. | Th. | Fd. | Th. | Fd. | Th. | Fd. | Th. |
| 43.21 | 43.05 | 7.97 | 7.94 | 32.71 | 32.86 | 8.02 | 7.94 |

$^{13}$C NMR analysis confirms the expected chemical structure, i.e.:

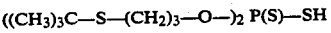
((CH$_3$)$_3$C—S—(CH$_2$)$_3$—O—)$_2$ P(S)—SH

EXAMPLE 2

Synthesis of a monosulphurized zinc dialkyldithiophosphate (known product)

Part of the previously obtained sulphurized dialkylthiophosphoric acid (30 g, i.e. 0.077 mole) is transformed into sodium salt by adding to it 100 cm$^3$ of an aqueous sodium solution (NaOH=3.2 g, i.e. 0.08 mole). This sodium salt is purified by successive extractions with hexane and then the recovered purified aqueous solution is treated with a solution of 12.66 g (0.045 mole) of 7H$_2$O ZnSO$_4$ dissolved in 30 cm$^3$ of water. The sulphurized zinc dialkyldithiophosphate then precipitates immediately. The mixture is extracted with chloroform, the organic phase recovered is dried on anhydrous Na$_2$SO$_4$ and then the solvent is eliminated by evaporating under reduced pressure. In this way 20.3 g of a viscous yellow liquid are collected, which is in accordance with the following elementary analysis:

| wt. % C | | wt. % H | | wt. % S | | wt. % P | | wt. % Zn | |
|---|---|---|---|---|---|---|---|---|---|
| Fd. | Th. | Fd. | Th. | Fd. | Th. | Fd. | Th. | Fd. | Th. |
| 40.11 | 39.81 | 7.26 | 7.11 | 30.69 | 30.40 | 7.24 | 7.35 | 7.82 | 7.75 |

Moreover, the infrared, $^{31}$P and $^{13}$C NMR analyses confirm the expected chemical structure of the zinc salt, i.e.:

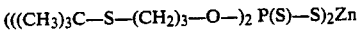
(((CH$_3$)$_3$C—S—(CH$_2$)$_3$—O—)$_2$ P(S)—S)$_2$Zn

EXAMPLE 3

Synthesis of a monosulphurized dialkyldithiophosphoric alcohol

Part of the sulphurized dialkyldithiophosphoric acid obtained in Example 1 (60 g, i.e. 0.154 mole) is introduced into a 250 cm$^3$ three-necked reactor, followed by the progressive addition of 10 g (0.172 mole) of epoxypropane, whilst not exceeding a reaction temperature of 30° C. After evaporating the excess epoxy propane under reduced pressure, 66 g of pale yellow liquid are recovered and the elementary analysis is as follows:

| wt. % C | | wt. % H | | wt. % S | | wt. % P | |
|---|---|---|---|---|---|---|---|
| Fd. | Th. | Fd. | Th. | Fd. | Th. | Fd. | Th. |
| 45.75 | 45.51 | 8.57 | 8.26 | 29.12 | 28.61 | 6.92 | 6.92 |

The infrared, $^{31}$P and $^{13}$C NMR analyses confirm the expected chemical structure, namely:

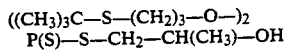
((CH$_3$)$_3$C—S—(CH$_2$)$_3$—O—)$_2$
P(S)—S—CH$_2$—CH(CH$_3$)—OH

EXAMPLE 4

Synthesis of a monosulphurized zinc dialkyldithiophosphyldithiophosphate

Into a 250 cm³ three-necked reactor equipped with a Dean-Stark separator, are introduced 1.7 g (0.016 mole) of sodium carbonate and 100 cm³ of benzene. The mixture is refluxed for 1 hour to make the medium anhydrous, followed by the addition of 3.66 g (0.0165 mole) of $P_2S_5$. This is followed by the progressive introduction of 29.6 g (0.066 mole) of monosulphurized dialkyldithiophosphoric alcohol prepared in Example 3. The mixture is then refluxed and kept there for 3 hours.

This is followed by cooling to 50° C. and the addition of 20 cm³ of ethyl alcohol containing 0.4 g (0.01 mole) of sodium hydroxide. Reaction is allowed to take place for 1 hour. Filtration takes place to eliminate the $P_2S_5$ in excess. This is followed by the addition of 50 cm³ of an aqueous solution containing 10 g of $7H_2O$ $ZnSO_4$ (0.0356 mole) and reaction is allowed to take place for 2 hours, accompanied by vigorous stirring. This is followed by drying on $Na_2SO_4$, filtering and evaporation of the benzene under reduced pressure. A pale viscous yellow liquid is recovered, which has the following elementary analysis:

| wt. % C | | wt. % H | | wt. % S | | wt. % P | | wt. % Zn | |
|---|---|---|---|---|---|---|---|---|---|
| Fd. | Th. | Fd. | Th. | Fd. | Th. | Fd. | Th. | Fd. | Th. |
| 40.01 | 39.91 | 7.27 | 7.04 | 30.89 | 31.36 | 8.95 | 9.10 | 3.06 | 3.20 |

The infrared, $^{31}P$ and $^{13}C$ NMR analyses confirm the expected chemical structure, namely:

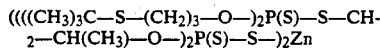

((((CH₃)₃C—S—(CH₂)₃—O—)₂P(S)—S—CH-2—CH(CH₃)—O—)₂P(S)—S—)₂Zn

EXAMPLE 5

Synthesis of a monosulphurized dialkyldithiophosphoric acid triester

In a first stage, 30 g (0.2 mole) of monosulphurized alcohol prepared in Example 1 are dissolved in 60 cm³ of chloroform, followed by the progressive addition of 11.9 g of $SOCl_2$ (0.1 mole). The mixture is then refluxed, followed by the progressive addition of 11.94 g of $SOCl_2$ (0.1 mole), followed by the maintenance of reflux for a further 2 hours. After cooling, the chloroform is eliminated by evaporation and the chlorine derivative corresponding to the monosulphurized alcohol is purified by distillation under reduced pressure (PE=92° C./1 mmbar), which gives 31.5 g of product (0.189 mole).

In a second stage, 27.3 g (0.07 mole) of monosulphurized dialkyldithiophosphoric acid prepared in Example 1 are transformed into sodium salt in the manner indicated in Example 2. The aqueous purified sodium salt solution is then mixed with 1 g of tetrabutyl ammonium hydrogen sulphate (phase transfer catalyst), followed by the addition of 11.42 g (0.07 mole) of the halogen-containing derivative of the preceding first stage dissolved in 10 cm³ of dichloromethane. The mixture is refluxed for 10 hours, cooled, the recovered organic phase washed with water, dried on $Na_2SO_4$, filtered and then evaporated under reduced pressure. In this way 35 g of product are recovered with the following elementary analysis:

| wt. % C | | wt. % H | | wt. % S | | wt. % P | |
|---|---|---|---|---|---|---|---|
| Fd. | Th. | Fd. | Th. | Fd. | Th. | Fd. | Th. |
| 48.78 | 48.43 | 8.57 | 8.65 | 31.02 | 30.81 | 6.04 | 5.96 |

The infrared, $^{31}P$ and $^{13}C$ NMR analyses confirm the expected chemical structure, namely:

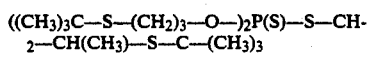

((CH₃)₃C—S—(CH₂)₃—O—)₂P(S)—S—CH-2—CH(CH₃)—S—C—(CH₃)₃

EXAMPLE 6

Synthesis of monosulphurized dialkylchlorophosphates.

Example 6.1 (known product)

Into a 500 cm³ three-necked reactor are introduced 16 g (0.104 mole) of $POCl_3$ dissolved in 50 cm³ of benzene. This is followed by the progressive addition of a solution constituted by 30.8 g (0.208 mole) of monosulphurized alcohol prepared in Example 1, 16 g of pyridine and 50 cm³ of benzene. The mixture obtained is stirred at ambient temperature for one hour. The pyridinium chloride obtained is eliminated by filtration, the organic phase washed with water, dried on $Na_2SO_4$ and evaporated under reduced pressure. This gives 38 g of product with the following elementary analysis:

| wt. % C | | wt. % H | | wt. % S | | wt. % P | | wt. % Cl | |
|---|---|---|---|---|---|---|---|---|---|
| Fd | Th | Fd | Th | Fd | Th | Fd | Th | Fd | Th. |
| 44.89 | 44.61 | 8.02 | 7.97 | 17.44 | 17.03 | 8.11 | 8.23 | 9.65 | 9.43 |

The infrared, $^{31}P$ and $^{13}C$ NMR analyses confirm the expected chemical structure:

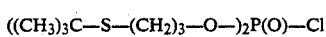

((CH₃)₃C—S—(CH₂)₃—O—)₂P(O)—Cl

Example 6.2: (novel product)

The same experiment performed on the basis of the monosulphurized thiophosphorus alcohol prepared in Example 3 leads to a product corresponding to the following formula:

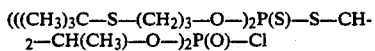

(((CH₃)₃C—S—(CH₂)₃—O—)₂P(S)—S—CH-2—CH(CH₃)—O—)₂P(O)—Cl

EXAMPLE 7

Synthesis of monosulphurized zinc dialkylphosphates

Example 7.1 (known product)

In a first stage vigorous stirring takes place of 18 g (0.048 mole) of the first monosulphurized dialkylchlorophosphate obtained in Example 6 with 50 cm³ of an aqueous 2N sodium solution for 2 hours, followed by the extraction of the mixture with toluene. The recovered aqueous phase is acidified with 2N hydrochloric acid, extracted with toluene, washed with water, dried on $Na_2SO_4$, filtered and then evaporated under reduced pressure. This gives 15 g of a yellow liquid with the following elementary analysis:

| wt. % C | | wt. % H | | wt. % S | | wt. % P | |
| --- | --- | --- | --- | --- | --- | --- | --- |
| Fd | Th | Fd | Th | Fd | Th | Fd | Th. |
| 47.21 | 46.91 | 8,87 | 8.66 | 17.45 | 17.91 | 8.44 | 8.66 |

The infrared, $^{31}$P and $^{13}$C NMR analyses confirm the chemical structure of the expected monosulphurized dialkylphosphoric acid, namely:

$$((CH_3)_3C-S-(CH_2)_3-O-)_2P(O)-OH$$

In a second stage neutralization takes place of 15 g (0.042 mole) of monosulphurized dialkylphosphoric acid prepared in the preceding first stage with 2.35 g of potassium dissolved in 50 cm$^3$ of methyl alcohol. Stirring is maintained for 30 minutes at ambient temperature, followed by the addition of 12.7 g (0.045 mole) of 7H$_2$O ZnSO$_4$ dissolved in 25 cm$^3$ of water. The mixture is stirred for 30 minutes at ambient temperature, followed by extraction with ethyl alcohol. The recovered organic phase is washed with water, dried on Na$_2$SO$_4$, filtered and then evaporated under reduced pressure. This gives 15 g of a very viscous, opalescent liquid with the following elementary analysis:

| wt. % C | | wt. % H | | wt. % S | | wt. % P | | wt. % Zn | |
| --- | --- | --- | --- | --- | --- | --- | --- | --- | --- |
| Fd | Th | Fd | Th | Fd | Th | Fd | Th | Fd | Th. |
| 43.52 | 43.10 | 7.55 | 7.70 | 16.26 | 16.45 | 8.14 | 7.95 | 8.11 | 8.39 |

The infrared, $^{31}$P and $^{13}$C NMR analyses confirm the expected chemical structure, namely:

$$((CH_3)_3C-S-(CH_2)_3-O-)_2P(O)-O-)_2Zn$$

Example 7.2 (novel product)

The same experiment carried out on the basis of the chlorine derivative of the monosulphurized thiophosphorus alcohol prepared in Example 3 (cf. Example 6.1) leads to a product corresponding to the following formula:

$$((((CH_3)_3C-S-(CH_2)_3-O-)_2P(S)-S-CH_2-CH(CH_3)-O-)_2P(O)-O-)_2Zn$$

EXAMPLE 8

Synthesis of monosulphurized trialkylphosphates.

Example 8.1 (known product)

10 g (0.065 mole) of POCl$_3$ are dissolved in 50 cm$^3$ of benzene. The mixture is cooled to 5° C., followed by the progressive addition of a solution of 28.9 g (0.195 mole) of the monosulphurized alcohol prepared in Example 1, 30 g of pyridine and 50 cm$^3$ of benzene, whilst maintaining the reaction temperature at 5° C. Following addition, this temperature is maintained for a further 30 minutes. This is followed by heating to the reflux of the solvent and boiling is maintained for 2 hours. The solution is cooled, filtered, the organic phase washed with water, dried on Na$_2$SO$_4$, filtered and evaporated under reduced pressure. This gives 27 g of product with the following elementary analysis:

| wt. % C | | wt. % H | | wt. % S | | wt. % P | |
| --- | --- | --- | --- | --- | --- | --- | --- |
| Fd | Th | Fd | Th | Fd | Th | Fd | Th. |
| 51.87 | 51.62 | 9.54 | 9.22 | 19.22 | 19.70 | 6.11 | 6.35 |

The infrared, $^{31}$P and $^{13}$C NMR analyses confirm the expected chemical structure, namely:

$$((CH_3)_3C-S-(CH_2)_3-O-)_3P(O)$$

Example 8.2

The same experiment performed on the basis of the monosulphurized thiophosphorus alcohol prepared in Example 3 leads to a product corresponding to the following formula:

$$(((CH_3)_3C-S-(CH_2)_3-O-)_2P(S)-S-CH_2-CH(CH_3)-O-)_3P(O)$$

EXAMPLE 9

Synthesis of monosulphurized trialkylthiophosphates

EXAMPLE 9.1

The experiment of Example 8.1 is repeated substituting the POCl$_3$ by the same molar quantity of PSCl$_3$. After reaction and treatments, 24 g of product are collected with the following elementary analysis:

| wt. % C | | wt. % H | | wt. % S | | wt. % P | |
| --- | --- | --- | --- | --- | --- | --- | --- |
| Fd | Th | Fd | Th | Fd | Th | Fd | Th. |
| 50.12 | 49.97 | 9.01 | 8.92 | 25.12 | 25.43 | 6.11 | 6.15 |

The infrared, $^{31}$P and $^{13}$C NMR analyses confirm the expected chemical structure, namely:

$$((CH_3)_3C-S-(CH_2)_3-O-)_3P(S)$$

EXAMPLE 9.2

The same experiment performed on the basis of the monosulphurized thiophosphorus alcohol prepared in Example 3 leads to a product corresponding to the following formula:

$$(((CH_3)_3C-S-(CH_2)_3-O-)_2P(S)-S-CH_2-CH(CH_3)-O-)_3P(S)$$

EXAMPLE 10

Synthesis of monosulphurized dialkylphosphonates

EXAMPLE 10.1

30 g (0.18 mole) of monosulphurized alcohol prepared in Example 1 are dissolved in 100 cm$^3$ of carbon tetrachloride. Then, at ambient temperature, progressive addition takes place of 8.25 g (0.06 mole) of PCl$_3$ dissolved in 50 cm$^3$ of carbon tetrachloride. Boiling takes place and this temperature is maintained for 1 hour. The solvent is eliminated by evaporating under reduced pressure and the dialkylphosphonate is separated from the halogen-containing derivative by liquid silica column chromatography. This gives 18 g of product with the following elementary analysis:

| wt. % C | | wt. % H | | wt. % S | | wt. % P | |
|---|---|---|---|---|---|---|---|
| Fd | Th | Fd | Th | Fd | Th | Fd | Th. |
| 49.32 | 49.08 | 9.21 | 9.06 | 18.62 | 18.74 | 8.95 | 9.06 |

The infrared, $^{31}P$ and $^{13}C$ NMR analyses confirm the expected chemical structure, namely:

$((CH_3)_3C\text{—}S\text{—}(CH_2)_3\text{—}O\text{—})_2P(O)\text{—}H$

EXAMPLE 10.2

The same experiment, carried out on the basis of the monosulphurized thiophosphorus alcohol prepared in Example 3, leads to a product corresponding to the following formula:

$(((CH_3)_3C\text{—}S\text{—}(CH_2)_3\text{—}O\text{—})_2P(S)\text{—}S\text{—}CH_2\text{—}CH(CH_3)\text{—}O\text{—})_2P(O)\text{—}H$ These experiments (or syntheses) can be repeated using polysulphurized alcohols (x>1). In this way it is possible to regulate at random the sulphur quantity contained in the additives according to the invention and therefore obtain products having regulatable antiwear and extreme-pressure properties. The following examples illustrate these possibilities.

EXAMPLE 11

Synthesis of a polysulphurized alcohol

Into a 500 cm$^3$ three-necked reactor are introduced 200 cm$^3$ of methyl alcohol and then 44 g (1.1 mole) of sodium hydroxide. After dissolving, the mixture is heated to 50° C., followed by the progressive addition of 99 g (1.1 mole) of 2-methyl-2-propane-thiol. At the end of addition, the temperature is maintained at 50° C. for a further 30 minutes. This is followed by the progressive addition of 33.2 g (1.1 gramme atom) of elementary sulphur, then reaction is allowed to take place at 50° C. until the sulphur is completely dissolved. This is followed by the progressive introduction of 92.5 g (1 mole) of n-chloropropanol. The mixture is heated to the reflux of the alcohol for 6 hours and then cooled to ambient temperature.

The NaCl formed is eliminated by filtration and the organic solution evaporated under reduced pressure. The organic phase is washed with water to eliminate the toluene-extracted sodium polysulphide excess, dried on Na$_2$SO$_4$ and evaporated under reduced pressure. The crude polysulphurized alcohol obtained is purified by liquid chromatography on silica, whilst eluting the impurities with hexane (tert. butyl polysulphides), the desired product then being recovered by eluting with methyl alcohol. After evaporating the methyl alcohol, in this way 173 g of polysulphurized tert. butyl alcohol are recovered with the following elementary analysis:

| wt. % C | | wt. % H | | wt. % S | |
|---|---|---|---|---|---|
| Fd | Th | Fd | Th | Fd | Th |
| 46.87 | 46.63 | 8.92 | 8.88 | 35.24 | 35.60 |

The infrared, $^{31}P$ and $^{13}C$ NMR analyses confirm the expected chemical structure, namely a statistical mixture of sulphurized alcohols of the following summary formula:

$(CH_3)_3C\text{—}S_2\text{—}(CH_2)_3\text{—}OH$

EXAMPLE 12

Synthesis of a polysulphurized dialkyldithiophosphoric acid

Into a 1000 cm$^3$ three-necked reactor are introduced 150 g (0.83 mole) of polysulphurized alcohol prepared in Example 11 and 400 cm$^3$ of chloroform. The mixture is heated to 60° C., followed by the progressive addition of 46.11 g (0.207 mole) of P$_2$S$_5$. After complete dissolving of the P$_2$S$_5$, the mixture is kept for an additional hour at 60° C., accompanied by stirring. After eliminating the chloroform under reduced pressure, 185 g of pale yellow liquid are collected with the following elementary analysis:

| wt. % C | | wt. % H | | wt. % S | | wt. % P | |
|---|---|---|---|---|---|---|---|
| Fd | Th | Fd | Th | Fd | Th | Fd | Th. |
| 37.12 | 36.97 | 6.92 | 6.82 | 42.11 | 42.34 | 6.71 | 6.82 |

The infrared, $^{31}P$ and $^{13}C$ NMR analyses confirm the expected chemical structure, namely:

$((CH_3)_3C\text{—}S_2\text{—}(CH_2)_3\text{—}O\text{—})_2P(S)\text{—}SH$

EXAMPLE 13

Synthesis of a polysulphurized dialkyldithiophosphoric alcohol 100 g of polysulphurized dialkyldithiophosphoric acid obtained in Example 12 (0.22 mole) are introduced into a 500 cm$^3$ three-necked reactor, followed by the progressive addition of 15 g (0.26 mole) of epoxy propane, whilst not exceeding a reaction temperature of 30° C. After reducing the excess epoxy propane under reduced pressure, 112 g of pale yellow liquid are recovered with the following elementary analysis:

| wt. % C | | wt. % H | | wt. % S | | wt. % P | |
|---|---|---|---|---|---|---|---|
| Fd | Th | Fd | Th | Fd | Th | Fd | Th |
| 39.94 | 39.81 | 7.35 | 7.22 | 37.32 | 37.55 | 6.01 | 6.05 |

The infrared, $^{31}P$ and $^{13}C$ NMR analyses confirm the expected chemical structure of the alcohol, namely:

$((CH_3)_3C\text{—}S_2\text{—}(CH_2)_3\text{—}O\text{—})_2P(S)\text{—}S\text{—}CH_2\text{—}CH(CH_3)\text{—}OH$

EXAMPLE 14

Synthesis of polysulphurized zinc dialkyldithiophosphate

The experiments of Examples 1 and 2 are repeated with the polysulphurized alcohol prepared in Example 11. Following the reactions and separation, a polysulphurized zinc dialkyldithiophosphate with the following elementary analysis is obtained:

| wt. % C | | wt. % H | | wt. % S | | wt. % P | | wt. % Zn | |
|---|---|---|---|---|---|---|---|---|---|
| Fd | Th | Fd | Th | Fd | Th | Fd | Th | Fd | Th |
| 34.82 | 34.56 | 6.37 | 6.17 | 39.21 | 39.58 | 6.14 | 6.38 | 6.46 | 6.73 |

The infrared, $^{31}P$ and $^{13}C$ NMR analyses confirm the expected chemical structure of the product, namely:

as a function of the value chosen for x (1,2,3 etc). This improvement can be advantageously used in the formulation of lubricating oils, especially for gears.

TABLE 1

| Additive of Example | S quantity in additive wt. % | Additive quantity in oil wt. % | S quantity in oil wt. % | Extreme-Pressure | | | | | | Wear Impression diameter (mm) 1 h under load of | | |
|---|---|---|---|---|---|---|---|---|---|---|---|---|
| | | | | Wear load value | | Load before seizing | | Welding load | | 40 kgf 392.4 Newt | 60 kfg 588.6 Newt | 80 kgf 784.8 Newt |
| | | | | kgf | Newt | kgf | Newt | kgf | Newt | | | |
| — | — | — | — | 28.0 | 274.7 | 50 | 490.5 | 150 | 1471.5 | 1.47 | 1.90 | 2.50 |
| 2 | 30.69 | 0.652 | 0.2 | 36.0 | 353.2 | 80 | 784.8 | 200 | 1962.0 | 0.36 | 0.68 | 0.98 |
| 14 | 39.21 | 0.510 | 0.2 | 55.4 | 543.5 | 126 | 1236.1 | 250 | 2452.5 | 0.33 | 0.60 | 0.87 |
| 4 | 30.89 | 0.647 | 0.2 | 42.9 | 420.8 | 100 | 981.0 | 200 | 1962.0 | 0.45 | 0.66 | 0.98 |
| 15 | 38.67 | 0.517 | 0.2 | 47.0 | 461.1 | 100 | 981.0 | 250 | 2452.5 | 0.37 | 0.65 | 0.90 |
| 3 | 29.12 | 0.755 | 0.22 | 34.9 | 342.4 | 80 | 784.8 | 200 | 1962.0 | 0.35 | 0.52 | 1.10 |
| 5 | 31.02 | 0.709 | 0.22 | 33.8 | 331.6 | 80 | 784.8 | 200 | 1962.0 | 0.36 | 0.55 | 1.07 |
| 8.1 | 19.22 | 1.116 | 0.22 | 35.9 | 352.2 | 80 | 784.8 | 200 | 1962.0 | 0.39 | 0.67 | 0.93 |
| 9.1 | 25.12 | 0.875 | 0.22 | 42.9 | 420.8 | 100 | 981.0 | 250 | 2452.5 | 0.37 | 0.61 | 0.90 |
| 10.1 | 18.62 | 1.182 | 0.22 | 50.6 | 496.4 | 126 | 1236.1 | 200 | 1962.0 | 0.42 | 0.48 | 1.20 |
| 11 | 35.24 | 0.624 | 0.22 | 37.2 | 364.9 | 80 | 784.8 | 200 | 1962.0 | 0.39 | 0.54 | 1.09 |

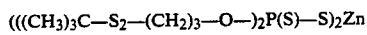

$(((CH_3)_3C-S_2-(CH_2)_3-O-)_2P(S)-S)_2Zn$

EXAMPLE 15

Synthesis of a polysulphurized zinc dialkyldithiophosphyl dithiophosphate

The experiment of Example 4 is repeated with the polysulphurized dialkyldithiophosphoric alcohol prepared in Example 13. Following reactions and separation, a polysulphurized zinc dialkyldithiophosphyl dithiophosphate is obtained with the following elementary analysis:

| wt. % C | | wt. % H | | wt. % S | | wt. % P | | wt. % Zn | |
|---|---|---|---|---|---|---|---|---|---|
| Fd | Th | Fd | Th | Fd | Th | Fd | Th | Fd | Th |
| 35.58 | 35.46 | 6.46 | 6.26 | 38.67 | 39.01 | 7.95 | 8.08 | 2.64 | 2.84 |

The infrared, $^{31}P$ and $^{13}C$ NMR analyses confirm the chemical structure of the product, namely:

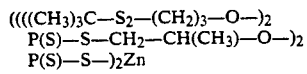

$((((CH_3)_3C-S_2-(CH_2)_3-O-)_2$
$P(S)-S-CH_2-CH(CH_3)-O-)_2$
$P(S)-S-)_2Zn$

Evaluation of the extreme-pressure and antiwear properties of the additives according to the invention.

Tests are carried out to reveal the antiwear and extreme-pressure properties of the additives according to the invention in lubricating formulations of the gear oil type.

The additives of Examples 2,3,4,5,8.1,9.1,10.1,11,14 and 15 were studied with the aid of a machine with four balls according to the procedure of ASTM D 2783 at concentrations such that the sulphur content of the mineral-based oil SAE 80W90 is equal to or close to 0.2% by weight. The results obtained are given in Table 1.

It can in particular be seen that the functional additives according to the invention have good antiwear and extreme-pressure properties, which can be modified as a function of the sulphur quantity used in the syntheses. It can also be seen that for the same sulphur concentration the polysulphide-type additives (in this case x=2) generally have better performance characteristics than the monosulphide-type additives (x=1), which gives the possibility of regulating at random the mechanical performance characteristics of these products,

EXAMPLE 16

Synthesis of the compound

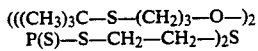

$(((CH_3)_3C-S-(CH_2)_3-O-)_2$
$P(S)-S-CH_2-CH_2-)_2S$ a-First stage, preparation of the monosulphurized alcohol:

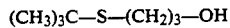

$(CH_3)_3C-S-(CH_2)_3-OH$ 150 cm³ of pure ethyl alcohol are introduced into a 500 cm³ three-necked reactor, followed by 18.6 g (0.465 g-mole) of sodium hydroxide. After dissolving, the mixture is heated to 50° C., followed by the progressive addition of 41.9 g (0.465 g-mole) of 2-methyl-2-propane thiol. At the end of addition, the temperature is kept at 50° C. for a further 30 minutes, followed by cooling to 20° C. This is followed by the progressive addition of 43.95 g (0.465 g-mole) of n-chloropropanol, the mixture then being heated to the reflux of alcohol for 6 hours, followed by cooling to ambient temperature.

The NaCl formed is eliminated by filtration and the organic solution acidified by a 2N HCl aqueous solution. The organic phase is collected and then the aqueous phase extracted by dichloromethane. The organic fractions are combined, washed with water, dried on anhydrous $Na_2SO_4$ and the dichloromethane is eliminated by evaporation under reduced pressure.

The purification of the sulphur-containing alcohol takes place by distillation under reduced pressure (PE=84° C./1 mbar). 68.5 g of colourless product are recovered with the following elementary analysis:

| wt. % C | | wt. % H | | wt. % S | |
|---|---|---|---|---|---|
| Fd | Th | Fd | Th | Fd | Th |
| 56.81 | 56.73 | 10.79 | 10.81 | 21.84 | 21.66 |

The infrared, $^1H$ and $^{13}C$ NMR analyses confirm the chemical structure of the product.

b-Second stage, preparation of a monosulphurized dialkyldithiophosphoric acid:

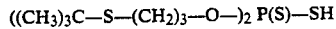

$((CH_3)_3C-S-(CH_2)_3-O-)_2 P(S)-SH$

Into a 250 cm³ reactor are introduced 19.0 g (0.128 g-mole) of monosulphurized alcohol prepared in the first stage and 40 cm³ of chloroform. The mixture is heated to 60° C., followed by the progressive addition of 7.11 g (0.032 g-mole) of P₂S₅. After complete dissolving, the mixture is kept for an additional hour at 60° C. and accompanied by stirring. After eliminating the chloroform under reduced pressure, 24 g of a pale yellow liquid are obtained with the following elementary analysis:

| wt. % C | | wt. % H | | wt. % S | | wt. % P | |
|---|---|---|---|---|---|---|---|
| Fd | Th | Fd | Th | Fd | Th | Fd | Th |
| 43.21 | 43.05 | 7.97 | 7.94 | 32.71 | 32.86 | 8.02 | 7.94 |

The infrared, ¹H and ¹³C analyses confirm the expected chemical structure of the product.

c-Third stage, preparation of a monosulphurized dialkyldithiophosphoric alcohol:

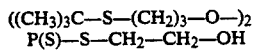
P(S)—S—CH₂—CH₂—OH

Into a 100 cm³ reactor are introduced 22.0 g (0.0564 g-mole) of sulphur-containing dialkyldithiophosphoric acid prepared in the preceding stage, followed by the addition of 2.8 g (0.064 g-mole) of ethylene oxide, accompanied by stirring and whilst vigorously cooling in order to maintain a temperature of 25° C. The ethylene oxide excess is eliminated by evaporation under reduced pressure and 24 g of a viscous liquid are collected having the following elementary analysis:

| wt. % C | | wt. % H | | wt. % S | | wt. % P | |
|---|---|---|---|---|---|---|---|
| Fd | Th | Fd | Th | Fd | Th | Fd | Th |
| 44.09 | 44.22 | 8.12 | 8.06 | 29.32 | 29.53 | 7.03 | 7.14 |

The infrared, ¹H, ³¹P and ¹³C NMR analyses confirm the expected chemical structure of the product.

d-Fourth stage, preparation of the chloride corresponding to the preceding monosulphurized dialkyldithiophosphoric alcohol:

((CH₃)₃C—S—(CH₂)₃—O—)₂
P(S)—S—CH₂—CH₂—Cl

Into a 100 cm³ reactor are introduced 20.0 g (0.046 g-mole) of monosulphurized dialkyldithiophosphoric alcohol prepared in the preceding stage, followed by the addition of 20 g of chloroform and then very progressively 2.74 g (0.023 g-mole) of SOCl₂, whilst maintaining the reaction temperature at about 20° C. The mixture is then refluxed and then very progressive addition again takes place of the same SOCl₂ quantity. After cooling, the chloroform is eliminated under reduced pressure in order to collect approximately 20 g of product, whose infrared, ³¹P, ¹H and ¹³C NMR analyses correspond to the expected chemical structure of the product.

e-Fifth and final stage, preparation of the sought compound:

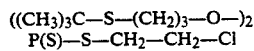
P(S)—S—CH₂—CH₂—)₂S

Into the reactor of the preceding stage are introduced 20 g of chloroform in order to dissolve the chlorine-containing derivative followed by 1 g of tetrabutyl ammonium chloride (phase transfer catalyst) and finally very progressive 20 cm³ of an aqueous solution containing 7 g of 9H₂O Na₂S (0.03 g-mole) whilst maintaining the temperature at about 20° C. The mixture is then refluxed for 1 hour, cooled and the phases separated. The recovered organic fraction is washed with water, dried on anhydrous NaSO₄ and then filtered to collect 19 g of product with the following elementary analysis:

| wt. % C | | wt. % H | | wt. % S | | wt. % P | |
|---|---|---|---|---|---|---|---|
| Fd | Th | Fd | Th | Fd | Th | Fd | Th |
| 44.89 | 44.31 | 7.99 | 7.85 | 32.47 | 33.30 | 7.01 | 7.15 |

The infrared, ¹H, ³¹P and ¹³C NMR analyses confirm the chemical structure of the product.

EXAMPLE 17

Synthesis of the compound

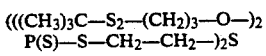
P(S)—S—CH₂—CH₂—)₂S

The first stage (a) of Example 16 is repeated, whilst adding to the reaction mixture 14.91 g (0.465 g-mole) of elementary sulphur in order to statistically form the disulphurized compound. After reaction, the crude disulphurized alcohol obtained is purified by liquid chromatography on silica gel, followed by elution with hexane in order to eliminate the impurities and with methyl alcohol which, after evaporation under reduced pressure, makes possible to recover the sought purified, disulphurized alcohol. The experiment is continued using the same molar proportions of reagents in order to obtain after the fifth stage (e) a product with the following elementary analysis:

| wt. % C | | wt. % H | | wt. % S | | wt. % P | |
|---|---|---|---|---|---|---|---|
| Fd | Th | Fd | Th | Fd | Th | Fd | Th |
| 38.97 | 38.60 | 7.05 | 6.84 | 41.02 | 41.90 | 6.01 | 6.23 |

The infrared, ³¹P and ¹³C NMR analyses correspond to the expected chemical structure of the product.

EXAMPLE 18

Synthesis of the compound ((CH₃)₃C—S—(CH₂)₃—O—)₂
P(S)—S—CH₂—CH₂—)₂S₂

The experiment of Example 16 is integrally repeated up to the fifth stage, where use is made of 25 cm³ of an aqueous solution containing 7 g of 9H₂O Na₂S (0.03 g-mole) and 1 g of elementary sulphur (0.03 g-atom) for statistically forming the disulphurized compound. This gives a product with the following elementary analysis:

| wt. % C | | wt. % H | | wt. % S | | wt. % P | |
|---|---|---|---|---|---|---|---|
| Fd | Th | Fd | Th | Fd | Th | Fd | Th |
| 43.22 | 42.73 | 7.85 | 7.57 | 34.89 | 35.68 | 6.73 | 6.90 |

The infrared, ³¹P, ¹H and ¹³C NMR analyses correspond to the chemical structure of the statistically expected product.

EXAMPLE 19

Synthesis of the compound

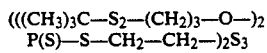
$P(S)-S-CH_2-CH_2-)_2S_3$

The experiment of Example 17 is repeated in order to prepare the sulphur-containing disulphurized dialkyldithiophosphorus alcohol. The experiment is continued, all molar proportions between the reagents being maintained, up to the fifth stage where use is made of 25 cm³ of an aqueous solution constituted by 7 g of 9H₂O Na₂S (0.03 g-mole) and 2 g of elementary sulphur (0.06 g-atom) in order to form the statistically sought trisulphurized compound. A product with the following elementary analysis is obtained:

| wt. % C | | wt. % H | | wt. % S | | wt. % P | |
|---|---|---|---|---|---|---|---|
| Fd | Th | Fd | Th | Fd | Th | Fd | Th |
| 36.86 | 36.26 | 6.78 | 6.42 | 44.71 | 45.42 | 5.34 | 5.85 |

The infrared, $^{31}P$, $^1H$ and $^{13}C$ NMR analyses correspond to the chemical structure of the statistically expected product.

Evaluation of the extreme-pressure and antiwear properties of the additives of Examples 16 to 19.

Tests are carried out to reveal the extreme-pressure and antiwear properties of the additives according to the invention using a machine with four balls according to the procedure of ASTM D 2783, under concentrations such that the sulphur content of the mineral oil SAE 80W90 is equal to 0.22% by weight. The results obtained are given in Table 2.

These results show that the additives according to the invention have good antiwear and extreme-pressure properties and that these can be modified as a function of the elementary sulphur quantity used in the syntheses. It is in particular shown that for an equal sulphur concentration, the compounds having polysulphide units are more effective than those having monosulphide units, which gives a possibility of regulating at random the mechanical performance characteristics of these products. This improvement can be used with advantage in the formulation of lubricating oils for gears or for the working of metals.

A represents the group $-(CH_2)_n-O-$ in which n is a number from 3 to 30; B represents the group

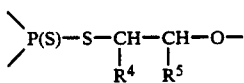

in which $R^4$ and $R^5$, which can be the same or different, in each case represent a hydrogen atom or a monovalent hydrocarbyl radical with 1 to 30 carbon atoms and $R^4$ and $R^5$ can be interlinked to form a polymethylene chain; X represents an oxygen atom or a sulphur atom; Y represents an oxygen atom, a sulphur atom, or a hydrocarbon chain interrupted by an oxygen or sulfur atom; Z represents a hydrogen atom, a chlorine atom, a sulphur atom, a polysulphide chain, a metal, an oxygen- or sulphur-containing derivative of molybdenum or a functionalized or non-functionalized alkyl or alkenyl $R^6$ group containing 1 to 30 carbon atoms; x is a number equal to or greater than 1; y is equal to 0,1 or 2; v is equal to 1; r is equal to 2; p is equal to 2 or 3; t is equal to 0 or 1; m is equal to 0,1 or 2; q is a number equal to the valency of Z if Z represents a metal or a number equal to 1 to 2, said functionalized alkyl or alkenyl $R^1$ and $R^6$ groups having at least one heteroatom selected from the group consisting of sulfur and chlorine, or at least one group selected from the group consisting of carboxylic, aldehyde, ketone, nitrile, hydroxyl and epoxide functions.

2. A phosphosulfur compound of claim 1 selected from:

(poly)sulfurized alcohols of general formula (III):

$$(R^1-S_x-(CH_2)_n-O-)_2P(S)-S-CH-CH-OH$$
$$\qquad\qquad\qquad\qquad\qquad\qquad R^7 \quad R^8$$

in which x is a number equal to or greater than 1, $R^7$ and $R^8$, which can be the same or different, in each case represent a hydrogen atom or a monovalent hydrocarbyl radical with 1 to 30 carbon atoms and $R^7$ and $R^8$ can be interlinked to form a polymethylene chain;

(poly)sulfurized dihydrocarbyldithiophosphyldithiophosphoric acid and the corresponding (poly)sulfurized metal salts of general formula (V):

TABLE 2

| Additive of Example | S quantity in additive wt. % | Additive quantity in oil wt. % | S quantity in oil wt. % | Extreme-Pressure | | | | | | Wear Impression diameter (mm) 1 h under load of | | |
|---|---|---|---|---|---|---|---|---|---|---|---|---|
| | | | | Wear load value | | Load before welding | | Welding load | | 40 Kgf | 60 Kfg | 80 Kgf |
| | | | | kgf | Newt | Kgf | Newt | Kgf | Newt | 392.4 Newt | 588.6 Newt | 784.8 Newt |
| — | — | 0 | — | 28.0 | 274.7 | 50 | 490.5 | 150 | 1471.5 | 1.47 | 1.90 | 2.50 |
| 16 | 32.47 | 0.68 | 0.22 | 33.8 | 331.6 | 80 | 784.8 | 200 | 1962.0 | 0.40 | 0.58 | 1.07 |
| 17 | 41.02 | 0.54 | 0.22 | 43.0 | 421.8 | 100 | 981.0 | 200 | 1962.0 | 0.39 | 0.55 | 0.98 |
| 18 | 34.89 | 0.63 | 0.22 | 36.0 | 353.2 | 80 | 784.8 | 200 | 1962.0 | 0.39 | 0.65 | 0.95 |
| 19 | 44.71 | 0.49 | 0.22 | 55.1 | 540.5 | 126 | 1236.1 | 250 | 2452.5 | 0.35 | 0.60 | 0.89 |

We claim:

1. A phosphosulfur compound in accordance with the following general formula (I):

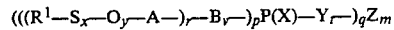

in which $R^1$ represents a functionalized or non-functionalized alkyl or alkenyl group with 1 to 30 carbon atoms;

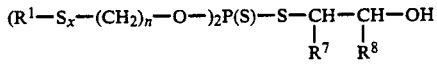

in which x is a number equal to or greater than 1, Z represents a hydrogen atom or a metal and q is equal to 1 if Z represents a hydrogen atom or equal to the valency of Z if Z is a metal;

(poly)sulfurized organic compounds of general formula (VII):

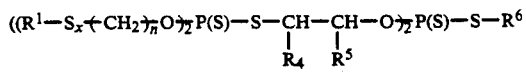

in which x is a number equal to or greater than 1;
(poly)sulfurized dihydrocarbyldithiophosphyl phosphoric acids and the corresponding (poly)sulfurized metal salts of general formula (IX):

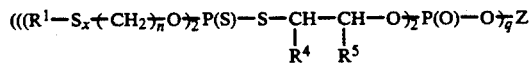

in which x is a number equal to or greater than 1, Z represents a hydrogen atom or a metal and q is equal to 1 if Z represents a hydrogen atom or equal to the valency of Z if Z is a metal;
(poly)sulfurized organic compounds of general formula (XII):

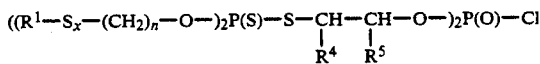

in which x is a number equal to or greater than 1; the organic compounds of general formula (XIII):

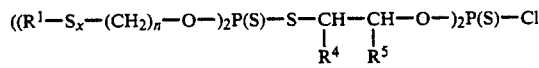

in which x is a number equal to or greater than 2; organic compounds of general formula (XV):

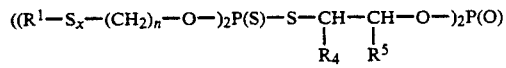

in which x is a number equal to or greater than 1; organic compounds of general formula (XVII):

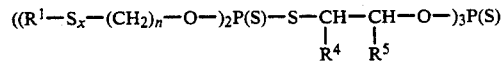

in which x is a number equal to or greater than 1; and
(poly)sulfurized organic compounds of general formula (XIX):

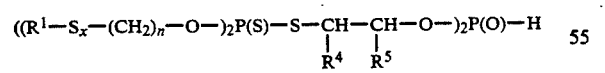

in which x is a number equal to or greater than 1.

3. A compound according to claim 1, wherein n is 3.
4. A compound according to claim 2, wherein n is 3.
5. A compound according to claim 1, wherein x is at least 2.
6. A compound according to claim 2, wherein x is at least 2.
7. A compound according to claim 3, wherein x is at least 2.
8. A compound according to claim 4, wherein x is at least 2.

9. A compound according to claim 1, wherein $R^1$ and $R^6$ are non-functionalized.

10. A compound according to claim 1, wherein at least one of $R^1$ and $R^6$ is functionalized.

11. A mineral-based lubricating oil containing a dissolved amount of a compound according to claim 1 in a concentration sufficient to improve the anti-wear properties of the lubricating oil.

12. A mineral-based lubricating oil containing a dissolved amount of a compound according to claim 2 in a concentration sufficient to improve the anti-wear properties of the lubricating oil.

13. A mineral-based lubricating oil containing a dissolved amount of a compound according to claim 11 in a concentration sufficient to improve the anti-wear properties of the lubricating oil.

14. A mineral-based lubricating oil containing a dissolved amount of a compound according to claim 12 in a concentration sufficient to improve the anti-wear properties of the lubricating oil.

15. A polysulfurized organic compound of formula XX:

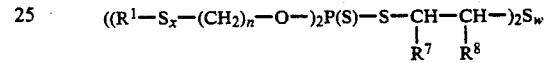

in which X is greater than or equal to 1, n is greater than or equal to 3, w is greater than or equal to 1, at least one of x or w being greater than 1, in which $R^1$ represents a functionalized or non-functionalized alkyl or alkenyl group with 1 to 30 carbon atoms; $R^7$ and $R^8$, which can be the same or different, in each case represent a hydrogen atom or a monovalent hydrocarbyl radical with 1 to 30 carbon atoms and $R^7$ and $R^8$ can be interlinked to form a polymethylene chain.

16. A compound according to claim 2 of the formula:

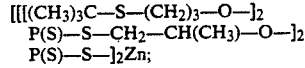

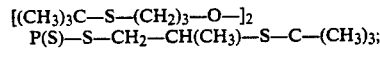

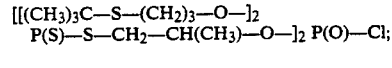

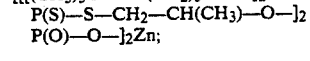

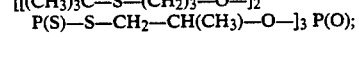

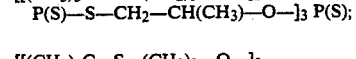

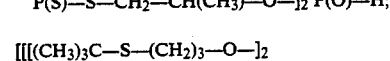

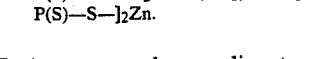

17. A compound according to claim 15, of the formula

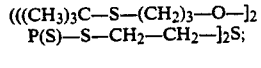

$(((CH_3)_3C-S-(CH_2)_3-O-]_2$
$P(S)-S-CH_2-CH_2-]_2S_2;$ $[((CH_3)_3C-S-(CH_2)_3-O-]_2$
$P(S)-S-CH_2-CH_2-]_2S_3;$ $[((CH_3)_3C-S_2-(CH_2)_3-O-]_2$
$P(S)-S-CH_2-CH_2-]_2S;$ $[((CH_3)_3C-S-(CH_2)_3-O-]_2$
$P(S)-S-CH_2-CH_2-]_2S_2;$ or $[((CH_3)_3C-S_2-(CH_2)_3-O-]_2$
$P(S)-S-CH_2-CH_2-]_2S_3.$

18. A (poly)sulfurized alcohol of general formula (III):

$$(R^1-S_x-(CH_2)_n-O-)_2P(S)-S-\underset{R^7}{CH}-\underset{R^8}{CH}-OH$$

in which x is a number equal to or greater than 1, $R^7$ and $R^8$, which can be the same or different, in each case represent a hydrogen atom or a monovalent hydrocarbyl radical with 1 to 30 carbon atoms or $R^7$ and $R^8$ can be interlinked to form a polymethylene chain;

in which $R^1$ represents a functionalized or non-functionalized alkyl or alkenyl group with 1 to 30 carbon atoms; and n is an integer from 1 to 30.

19. A compound according to claim 18 of the formula:

$[(CH_3)_3C-S-(CH_2)_3-O-]_2P(S)-S-CH_2-CH(CH_3)-OH;$ $[(CH_3)_3C-S-(CH_2)_3-O-]_2P(S)-S-CH_2-CH_2-OH.$ $[(CH_3)_3C-S_2-(CH_2)_3-O-]_2P(S)-S-CH_2-CH(CH_3)-OH.$

20. A mineral-based lubricating oil containing a dissolved amount of a compound according to claim 19 in a concentration sufficient to improve the anti-wear properties of the lubricating oil.

* * * * *